(12) United States Patent
Shoup et al.

(10) Patent No.: US 10,842,448 B2
(45) Date of Patent: Nov. 24, 2020

(54) DEVICE AND METHOD FOR DETERMINING PROPER SCREW OR IMPLANT SIZE DURING ORTHOPEDIC SURGERY

(71) Applicant: Surgentec LLC, Boca Raton, FL (US)

(72) Inventors: Andrew Shoup, Del Ray Beach, FL (US); Sean Biro, Boca Raton, FL (US); Walter Biro, Boca Raton, FL (US); Travis Greenhalgh, Boca Raton, FL (US)

(73) Assignee: SurGenTec LLC, Boca Raton, FL (US)

( * ) Notice: Subject to any disclaimer, the term of this patent is extended or adjusted under 35 U.S.C. 154(b) by 478 days.

(21) Appl. No.: 15/639,168

(22) Filed: Jun. 30, 2017

(65) Prior Publication Data
US 2019/0000405 A1    Jan. 3, 2019

(51) Int. Cl.
*A61B 6/12*    (2006.01)
*A61B 6/00*    (2006.01)
(Continued)

(52) U.S. Cl.
CPC ............... *A61B 6/12* (2013.01); *A61B 6/481* (2013.01); *A61B 6/487* (2013.01); *A61B 17/848* (2013.01); *A61B 17/8897* (2013.01); *A61B 17/3472* (2013.01); *A61B 17/8861* (2013.01); *A61B 17/92* (2013.01); *A61B 2017/00867* (2013.01); *A61B 2090/061* (2016.02); *A61B 2090/392* (2016.02); *A61B 2090/3966* (2016.02); *A61B 2090/3983* (2016.02)

(58) Field of Classification Search
CPC ......... A61B 6/12; A61B 6/487; A61B 17/848; A61B 17/8897; A61B 6/481; A61B 2090/061; A61B 2090/3966; A61B 17/92; A61B 17/8861; A61B 2090/3983; A61B 2090/392; A61B 17/3472; A61B 2017/00867
See application file for complete search history.

(56) References Cited

U.S. PATENT DOCUMENTS 6,241,690 B1 *   6/2001   Burkett ........... A61M 25/09025
                                                          600/585
6,428,512 B1 *   8/2002   Anderson ............. A61M 25/09
                                                          600/434
(Continued)

*Primary Examiner* — Sanjay Cattungal
(74) *Attorney, Agent, or Firm* — Kajane McManus; Jeanette M. Braun; Braun IP Law, LLC

(57) ABSTRACT

The devices and methods described herein refer to a guidewire, sometimes referred to as a K-wire, for use during varying orthopedic surgeries. The guidewire allows for the measurement of objects and distances inside the patient's body when used in tandem with x-ray or fluoroscopy imaging. Also, the devices and methods described herein act as a guide to accurately insert an instrument or implant, in the correct orientation, to the surgical site. The guidewire comprises a measurement segment that comprises one or more markers placed at known distances from the distal end of the guidewire. The markers, when used in tandem with fluoroscopy and/or x-ray imaging, provide users with a reference for measuring objects and distances inside the body. The markers can have many possible designs or configurations such as, but not limited to, visualization windows, grooves, notches, and/or material inserts.

31 Claims, 13 Drawing Sheets

(51) Int. Cl.
*A61B 17/88* (2006.01)
*A61B 17/84* (2006.01)
*A61B 17/00* (2006.01)
*A61B 17/34* (2006.01)
*A61B 90/00* (2016.01)
*A61B 17/92* (2006.01)

(56) References Cited

U.S. PATENT DOCUMENTS

| | | | | |
|---|---|---|---|---|
| 6,673,025 | B1* | 1/2004 | Richardson | A61M 25/09 600/585 |
| 7,637,934 | B2* | 12/2009 | Mangiardi | A61F 2/95 606/108 |
| 7,846,162 | B2* | 12/2010 | Nelson | A61B 17/7208 606/62 |
| 7,976,551 | B1* | 7/2011 | Gutfinger | A61B 5/0215 606/129 |
| 7,981,152 | B1* | 7/2011 | Webler | A61F 2/2451 623/2.36 |
| 2002/0193867 | A1* | 12/2002 | Gladdish, Jr. | A61L 31/022 623/1.15 |
| 2003/0088195 | A1* | 5/2003 | Vardi | A61B 5/1076 600/585 |
| 2003/0208142 | A1* | 11/2003 | Boudewijn | A61M 25/09 600/585 |
| 2004/0133129 | A1* | 7/2004 | Harari | A61B 5/1076 600/585 |
| 2005/0064223 | A1* | 3/2005 | Bavaro | A61B 5/6853 428/615 |
| 2005/0148902 | A1* | 7/2005 | Minar | A61L 31/10 600/585 |
| 2006/0155381 | A1* | 7/2006 | Katzman | A61F 2/3662 623/22.12 |
| 2007/0249964 | A1* | 10/2007 | Richardson | A61L 31/10 600/585 |
| 2008/0146967 | A1* | 6/2008 | Richardson | A61L 31/18 600/585 |
| 2008/0255447 | A1* | 10/2008 | Bourang | A61M 31/005 600/434 |
| 2009/0012612 | A1* | 1/2009 | White | A61F 2/30721 623/11.11 |
| 2010/0168864 | A1* | 7/2010 | White | A61B 50/30 623/18.11 |
| 2011/0301501 | A1* | 12/2011 | Tsunezumi | A61M 25/09 600/585 |
| 2012/0010619 | A1* | 1/2012 | Barsoum | A61B 17/16 606/79 |
| 2012/0022597 | A1* | 1/2012 | Gephart | A61B 17/7091 606/279 |
| 2015/0245882 | A1* | 9/2015 | Venkatraghavan | A61B 1/00009 600/424 |
| 2016/0196666 | A1* | 7/2016 | Venkatraghavan | G06T 7/254 382/130 |
| 2018/0185618 | A1* | 7/2018 | Sweeney | A61M 25/0662 |
| 2018/0199818 | A1* | 7/2018 | Belleville | A61M 25/09 |

* cited by examiner

DEVICE AND METHOD FOR DETERMINING PROPER SCREW OR IMPLANT SIZE DURING ORTHOPEDIC SURGERY

BACKGROUND

Field

The present disclosure generally relates to devices and methods for orthopedic surgery. More particularly, the present disclosure relates to devices and methods used to measure distances within and to aid in the insertion of instruments and implants into the body.

Description of the Related Art

Guidewires are used in many orthopedic procedures, especially in minimally invasive surgical procedures. In one example surgical procedure, a Jamshidi needle is used to create a pilot hole in the pedicle of a spinal vertebra. A guidewire is then inserted into the pilot hole and acts as a guide for pedicle screw placement to avoid injuring sensitive vascular or nerve tissue.

Currently available guidewires are made from many types of materials such as stainless steel, gold, platinum, titanium, tungsten, nickel, and alloys of such materials. Different materials provide for differences in stiffness, flexibility, and visual properties when under fluoroscopy or radiography. Since many orthopedic surgeries today are minimally invasive, fluoroscopy or x-ray imaging is needed to visualize structures and objects inside the body. The ability to visualize a guidewire under these types of imaging is dependent on the radiodensity of the material. Some materials are radiopaque, meaning they obstruct radiation from passing through them. A radiopaque material is visible on x-ray. On the contrary, a radiolucent material allows radiation to pass through it and is not visible on an x-ray. However, radiolucent materials may be "visualized" if they are surrounded by radiopaque material because of the contrast between the two materials.

Most guide wires currently available on the market are smooth elongated wires with one blunt end and either a sharp or blunt tip on the other side. Their main purpose is to act as a guide for implants or instruments into a desired location in the patient's body. Some of these guidewires may embody an extra feature, such as a depth stop, to prevent the guidewire from progressing past a certain depth in bone. A depth stop may be in the form of a projection off of the guidewire's body or in a change in diameter of the wire. In some cases, this type of feature may be limiting to the user if they need to go deeper than what the wire allows.

Some guidewires available today can be visualized inside the patient's body but they only provide users with information about relative position and orientation of the wire and surrounding objects. Some available guidewires may allow users to roughly measure a length of the guidewire within the patient's body through markings on the portion of the guidewire that remains outside of the body. However, these wires don't provide precise measurements because they do not allow the user to measure distances between structures or objects directly inside the patient's body. In a field where a millimeter could mean the difference between a successful surgery and a disaster, a rough estimate is not enough.

SUMMARY

During orthopedic surgery, it is vital to know the exact size of objects and distances inside the body to ensure no damage is done to sensitive tissues. Having the ability to accurately and precisely measure distances inside the body using a guidewire could be of great advantage to surgeons, patients, and hospitals. An example procedure which highlights these benefits well is the insertion of a pedicle screw into a vertebral body. Choosing the correct screw size isn't easy and errors in this process could be detrimental. A screw too short won't be stable and in turn may hinder the patient from healing. On the other hand, a screw too long can have life-threatening consequences such as nerve damage or hemorrhage. Getting the correct screw placement, especially on the first try, is of great benefit for the surgeon, patient, and hospital. If the screw size is incorrect, it must be extracted and a new one inserted. This causes further trauma to the patient, slowing their recovery, and can decreases the chances of the screw holding. Furthermore, once a screw is inserted into the body, it is no longer sterile and must be disposed of. This process is called explanting and it can cost hospitals tens of thousands of dollars annually. In addition, many fluoroscopy images are taken each time a surgeon attempts to place a screw, exposing both the surgeon and patient to potentially harmful radiation. It would therefore be beneficial to patients, surgeons, and hospitals to possess a guidewire that provides users the ability to accurately measure objects and distances inside the patient's body so they can get implant or instrument sizes correct on the first attempt.

The devices and methods described herein allow for the measurement of objects and distances inside the patient's body when used in tandem with x-ray or fluoroscopy imaging during orthopedic surgeries. Also, the devices and methods described herein act as a guide to accurately insert an instrument or implant, in the correct orientation, to the surgical site.

In some embodiments, the guide wire includes a wire body comprising a proximal end, a distal end, and one or more measurement segments. The wire body has one or more variable dimensions, rigidities, and/or radiodensities. The wire body is configured to fit inside the lumen of separately provided instruments or implants so such instruments or implants may slide distally along the guidewire to the surgical site. The distal end further comprises a tip configured to come into contact with the patient's tissue. The measurement segment comprises one or more markers configured to be visualized under fluoroscopy or x-ray imaging.

In some embodiments, the wire body is radiopaque and comprises a measurement segment with radiolucent markers. In other embodiments, the wire body is radiolucent and comprises a measurement segment with radiopaque markers. In some embodiments, the measurement segment is located on the distal portion of the wire body. In other embodiments, the measurement segment extends along the entire length of the wire body. In some embodiments, there are multiple measurement segments located along the wire body.

In one embodiment, the guidewire is made of nitinol, also known as nickel titanium. Nitinol is radiopaque and an excellent alloy for k-wires or guide wires because of its strength, biocompatibility, and kink resistant properties. In one embodiment, the nitinol wire has a measurement segment which comprises one or more visualization windows. These visualization windows are holes in the wire body that can be visualized while inside the body when used in tandem with x-ray or fluoroscopy. In one embodiment, the visualization windows are oval in shape and have a length of 6.6 $D_W \geq L_{VW} \geq 0.7\ D_W$, wherein $D_W$=Diameter of the wire body and $L_{VW}$=Length of the visualization window. In a wire with a diameter of 0.060 inches, this equates to a range of around 1 mm-10 mm which is an important size. Through multiple test methods, it was determined that the nitinol guidewire won't work for its intended use when the length of the visualization windows are outside that range. When the visualization window's length is smaller than 0.7 $D_W$ the side wall of the visualization window is too stiff and brittle. A brittle wire means an elevated risk of breaking and risk to patient's safety. On the other hand, when the visualization window's length is greater than 6.6 $D_W$, the side wall of the window becomes too flexible and causes the wire to bend too easily as it is inserted into the body. Also in one embodiment, there may be an alignment aid on the proximal tip of the guide wire. This alignment aid allows the user to line up the visualization windows so that the window is in the beam of the x-ray or fluoroscopy. It should be noted that in other embodiments, the visualization windows may be any shape and size, including but not limited to oval, triangular, square, rectangular, trapezoidal, pentagonal, hexagonal, or octagonal. In other embodiments, the visualization windows may be variably aligned in any access so that they may be visualized when the fluoroscopy or x-ray image is taken at any angle.

In some embodiments, the guidewire may be annealed or heat treated to change several of its properties including but not limited to the flexibility, strength, shape, color, biocompatibility, or chemical structure. Annealing can be a key manufacturing process to achieve the desired characteristics for differing surgeries. In some embodiments, different heating and cooling process may be used to make the guidewire more stiff, flexible, permanently bent in a given direction, etc.

In some embodiments, the guidewire may have visualization windows with lengths in the range of 1-10 mm. In another embodiment, the visualization windows may be in the range of 2-8 mm. In yet another embodiment, the visualization windows may be in the range of 5-8 mm. In some embodiments, the visualization windows may all have the same length and/or width. In other embodiments, the visualization windows may have varying lengths and/or widths. In one embodiment, the visualization windows of the guidewire span at least 10% of the wire's diameter which is important to allow the visualization windows to bend instead of break. When the visualization windows have a width less than 10% of the wire's diameter, the walls of the wire body that surround the visualization window are too stiff and brittle and can snap under significant pressure or flexing. Also, visualization windows less than 10% of the wire's diameter are difficult to visualize under fluoroscopy or x-ray when the wire diameter is an appropriate size for many orthopedic surgeries. When placing pedicle screws for instance, an average guide wire has a diameter less than or equal to 0.062". A visualization window less than or equal to 0.0062" would be very difficult to visualize.

In other embodiments, the visualization windows of the wire may be less than 1 mm or more than 10 mm. These embodiments would be designed for uses that don't put extreme forces on the wire.

In some embodiments, a method of guiding correctly sized implants or instruments to a desired location during orthopedic surgeries is described. A guidewire comprising a wire body with a proximal end, distal end, and one or more measurement segments is provided. The wire body can be made of a variety of materials to obtain one or more variable dimensions, rigidities, and/or radiodensities. The wire body can be configured to fit inside the lumen of separately provided instruments or implants. The distal end further comprises a tip configured to come into contact with the patient's tissue. The measurement segment comprises one or more markers configured to be visualized under fluoroscopy or x-ray imaging. The guidewire is inserted into the patient's body and the measurement segment is used, in tandem with separately provided fluoroscopy or x-ray imaging, to measure desired objects and distances within the patient's body. The guidewire is adjusted and temporarily positioned at the surgical site in the desired orientation and location. In some embodiments, the proximal end of the guidewire is inserted into the lumen of a separately provided implant or instrument which is progressed distally along the guidewire until in the desired location. The guidewire is removed after use.

In some embodiments, the wire may be used in a method of guiding correctly sized pedicle screws to a desired location during spinal surgeries. A guidewire comprising a wire body with a proximal end, distal end, and one or more measurement segments is provided. The wire body can be made of a variety of materials to obtain one or more variable dimensions, rigidities, and/or radiodensities. The wire body is configured to fit inside the lumen of separately provided pedicle screw and/or other instruments for the procedure such as a jamshidi needle. The distal end further comprises a tip configured to come into contact with the patient's tissue. The measurement segment comprises one or more markers configured to be visualized under fluoroscopy or x-ray imaging. The guidewire is inserted into the patient's pedicle and the measurement segment is used, in tandem with separately provided fluoroscopy or x-ray imaging, to determine the appropriate length pedicle screw necessary. A proximal end of the guidewire is then inserted into the lumen of a pedicle screw. The pedicle screw is then guided distally along the guidewire until in a desired location. The guidewire is then removed.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

The present disclosure is directed to methods and devices for a guidewire, often referred to as a k-wire, for orthopedic surgeries. The devices and methods described herein allow for the measurement of objects and distances inside a patient's body when used in tandem with x-ray or fluoroscopy imaging during orthopedic surgeries. The devices and methods described herein can also act as a guide to accurately insert an instrument or implant, in the correct orientation, to a surgical site by passing the instrument or implant over the guide wire. The devices described herein can be used in junction with a Jamshidi needle used to target and bore into bone while avoiding sensitive vascular and nerve tissue. Although some embodiments are described as being useful for surgeries requiring pedicle screw fixation, certain embodiments of this device may also apply to many other orthopedic surgeries that require a k wire or guide wire and could benefit from having distance markings which are able to be visualized under fluoroscopy.

Figure 1:
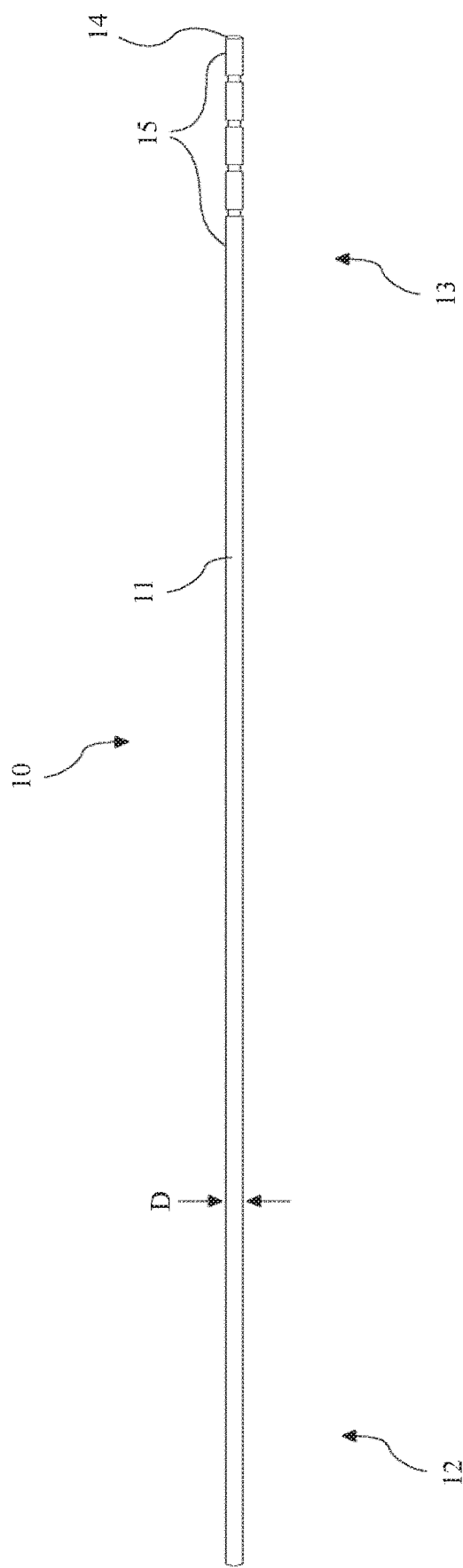
FIG. 1 depicts a full view of an example embodiment of a guidewire.

A full view of an example embodiment of a guidewire according to the present disclosure is depicted in FIG. 1. The guidewire (10) may be used during many types of orthopedic surgeries to act as a guide to the surgical site. The guidewire (10) comprises a wire body (11). The wire body (11) has a proximal end (12) and distal end (13). The distal end (13) can have a tip (14). In some embodiments, the wire body (11) may be radiopaque to allow users to visualize it inside the body when used in tandem with fluoroscopy or x-ray. As shown in FIG. 1, the wire body 11 can have variable dimensions. The term "dimensions" is used herein for convenience to describe both the width and depth of the wire body. The dimensions of the wire body (11) can be known by or provided to the user. In the illustrated embodiment, the wire body (11) has a circular cross-section. However, in other embodiments, the cross-section of the wire body (11) can be, for example without limitation, oval, triangular, square, rectangular, trapezoidal, pentagonal, hexagonal, or octagonal in shape. The guidewire (10) can advantageously allow users to measure objects and distances inside the body. The guidewire (10) includes a measurement segment (15). In the embodiment illustrated in FIG. 1, the measurement segment (15) is located on or proximate to the distal end (13). In some embodiments, the measurement segment (15) extends along the entire length of the wire body (11). When used in tandem with fluoroscopy, x-ray, or other appropriate imaging modalities, features of the measurement segment (15) stand out from the rest of the guidewire (10) or wire body (11). By varying the angle at which imaging is performed, users may accurately measure objects and distances inside the body in any dimension.

Figure 2:
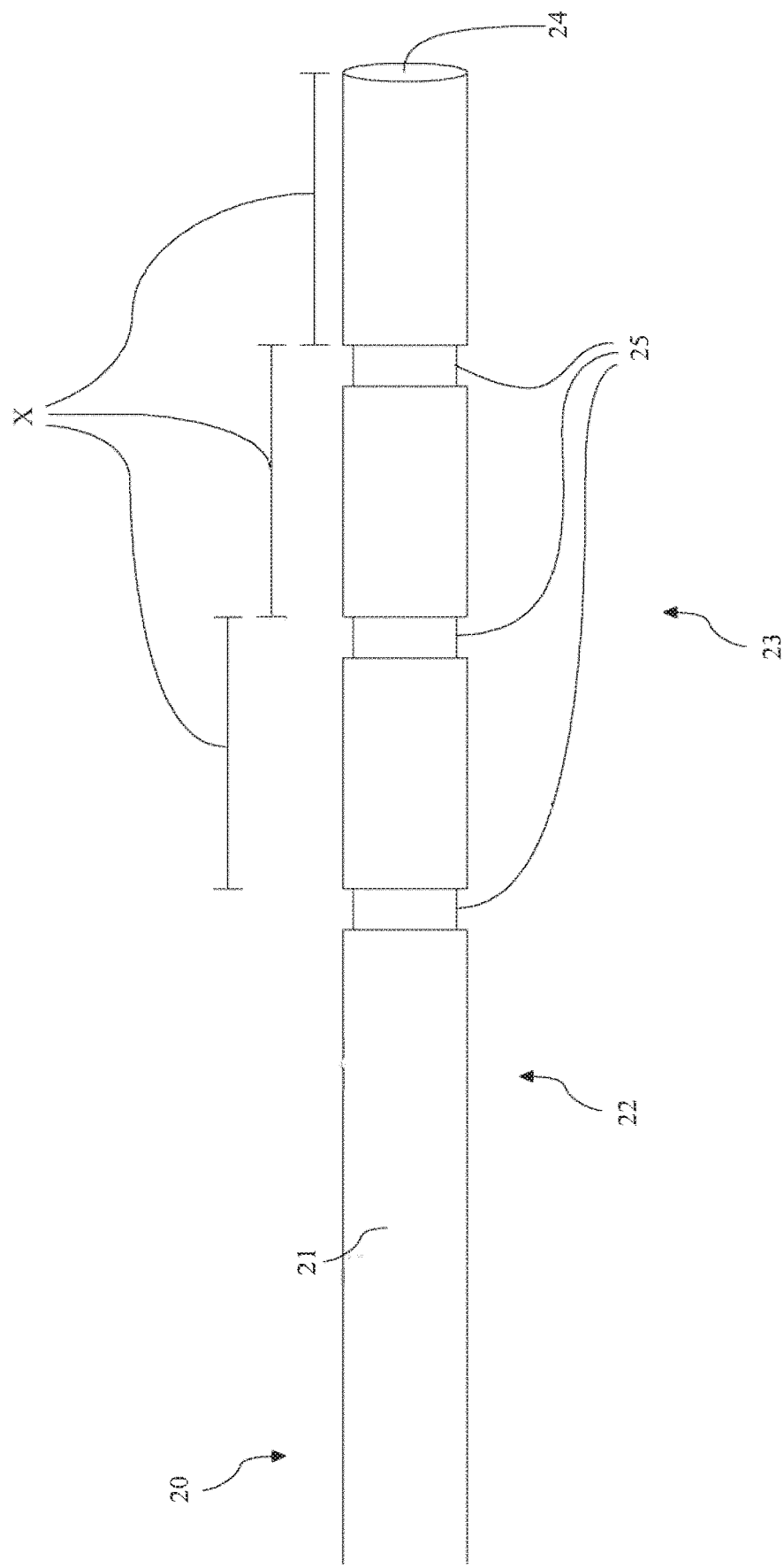
FIG. 2 depicts a detail view of a distal end of an example embodiment of a guidewire wherein the distal end comprises a measurement segment with evenly spaced grooves.

FIG. 2 depicts an example embodiment of a guidewire (20). FIG. 2 shows an enlarged view of a distal end (22) of a wire body (21) of the guidewire (20). As shown, the distal end (22) includes a measurement segment (23) and tip (24). In this embodiment, the measurement segment (23) includes one or more grooves (25). The one or more grooves (25) act as radiolucent markers under fluoroscopy or x-ray. The grooves (25) are uniformly spaced at set increments (X) to provide users a reference inside the body for measuring through comparison. The increments (X) may be 5 mm, 10 mm, or any size that fits the user's needs. It is a key feature of the guidewire (20) that the grooves (25) do not weaken the wire to a point where it can easily snap. Because the diameter of the grooves (25) is smaller than that of the wire body (21), the grooves (25) become a weak point of the guidewire (20). The grooves (25) are cut to a certain depth and angle to ensure the guidewire (20) is strong enough to withstand the forces put on it by the procedure. To also help ensure the grooves (25) are strong enough, a heating treating process may be performed.

Figure 3:
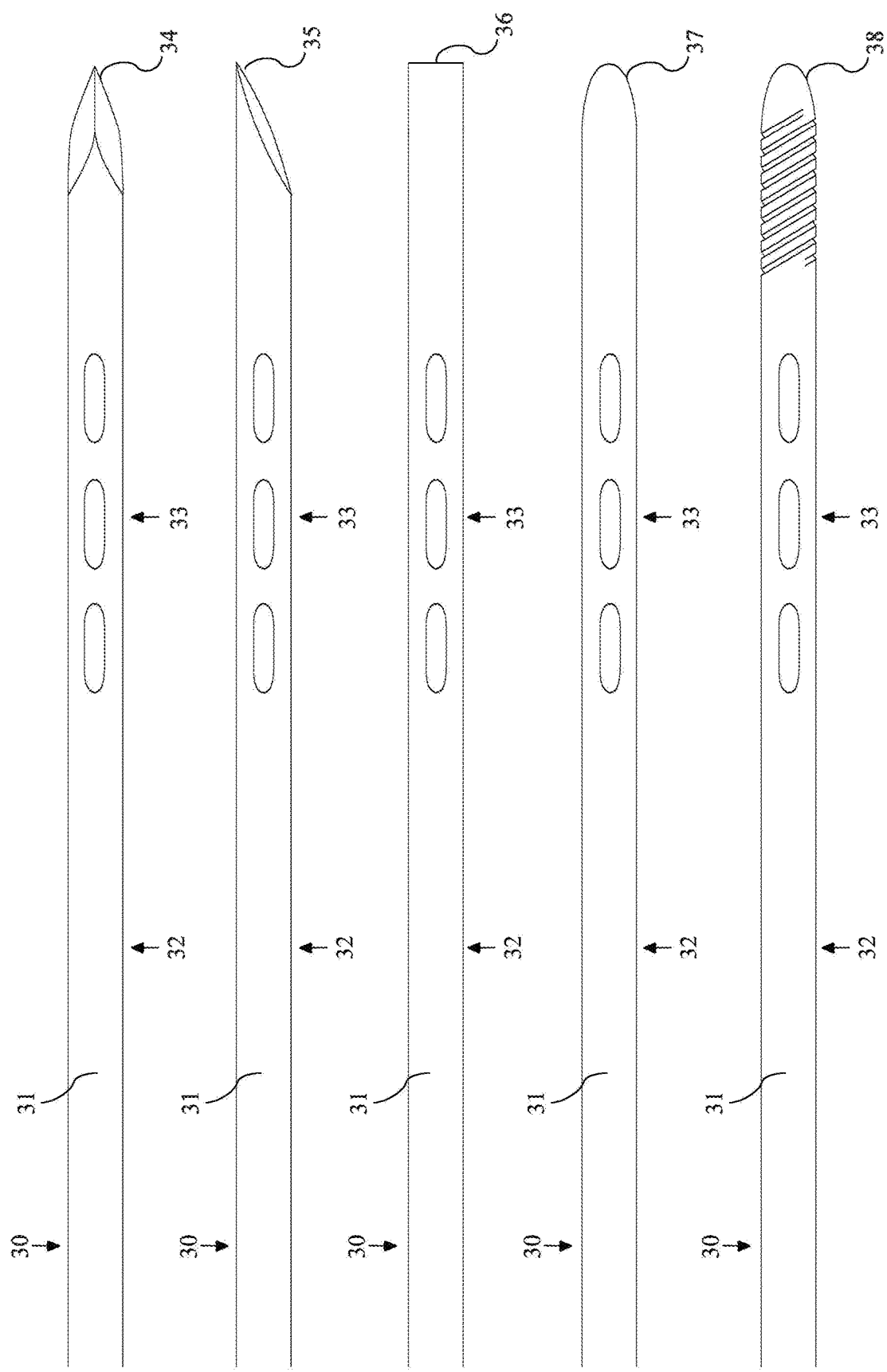
FIG. 3 depicts detail views of distal ends of several example embodiments of guidewires wherein the distal end comprises a tip that may be, but is not limited to, triangular, single beveled, squared, rounded or rounded with threads.

FIG. 3 depicts multiple example embodiments of a guidewire (30). FIG. 3 shows enlarged views of a distal end (32) of a wire body (31) of the guidewire (30). The distal end (32) includes a measurement segment (33). During orthopedic surgeries, the distal end (32) of the guidewire (30) must generally come into contact and travel through soft tissue and/or bone. In some embodiments, it is then advantageous for the guidewire (30) (i.e., the distal end (32)) to include a sharp single bevel tip (34) or triangular tip (35) to increase maneuverability through soft tissue and bone to the desired location. In many orthopedic surgeries, there are structures such as blood vessels and nerves close to the surgical site that if injured can be very serious or even fatal. For this reason, certain embodiments of the guidewire (30) include a blunt square tip (36) or rounded tip (37) to prevent or inhibit sensitive structures from being cut or punctured by a sharp tip. To accurately guide implants or instruments into the desired location, once the guidewire is in place it should not move. In one embodiment, the guidewire (30) comprises a rounded tip with threads (38) so that it may screw into bone at the desired location to prevent or inhibit the distal end (32) from relocating. Other tip styles or structures are also possible.

Figure 4:
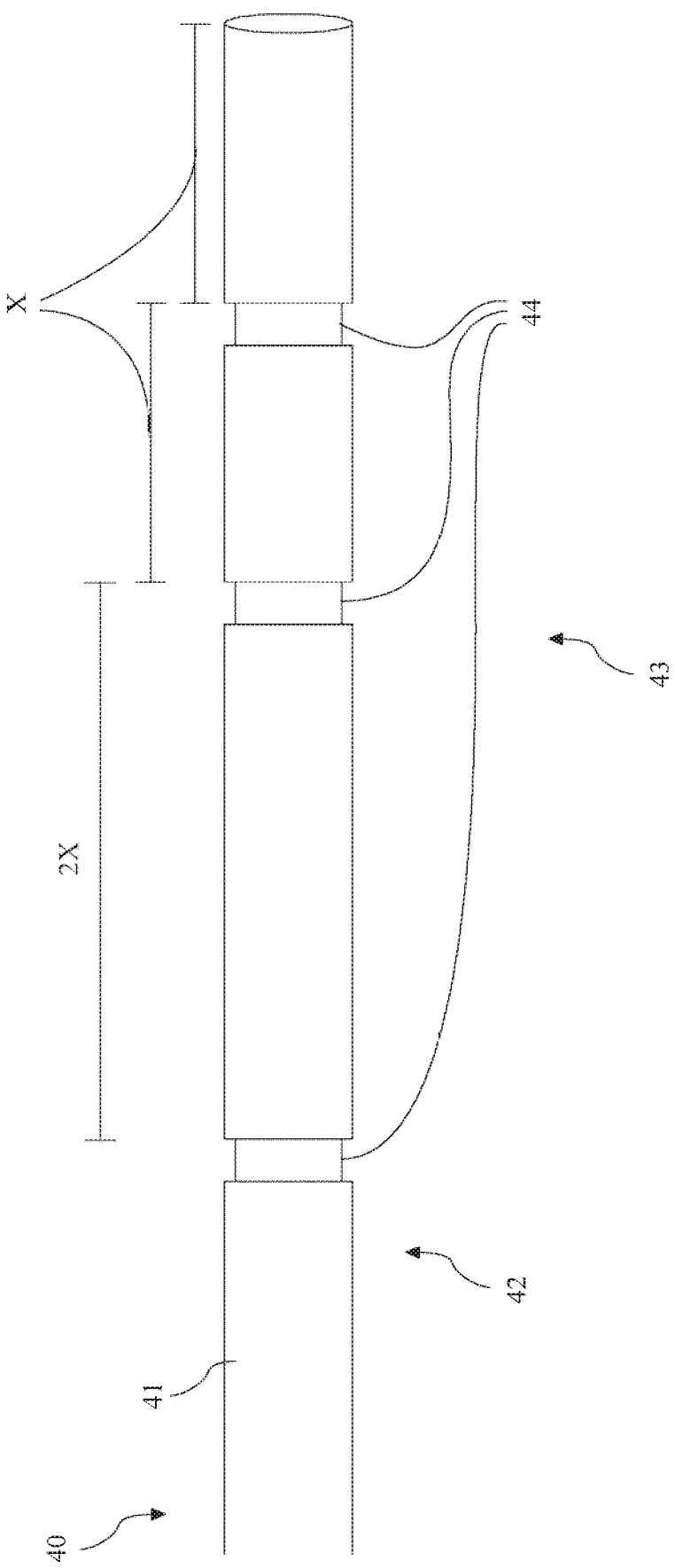
FIG. 4 depicts an example embodiment wherein the guidewire's distal end comprises a measurement segment with variably spaced grooves.

FIG. 4 depicts an example embodiment of a guidewire (40). FIG. 4 shows an enlarged view of a distal end (42) of a wire body (41) of the guidewire (40). The distal end (42)

includes a measurement segment (43). In this example embodiment, the measurement segment (43) includes one or more grooves (44). The grooves (44) can act as radiolucent markers under fluoroscopy or x-ray. In the illustrated embodiment, the grooves (44) are variably spaced at increments (X) or (2×) to allow users the ability to measure distances or objects inside the body. Having variably spaced grooves instead of uniformly spaced grooves may offer advantages such as fewer markers in the fluoroscopy or x-ray images, thus limiting crowding of the visual field or misinterpretation of markers. Other variably spaced increments such as, but not limited to, 1.5×, 3×, 4× are also possible.

Figure 5:
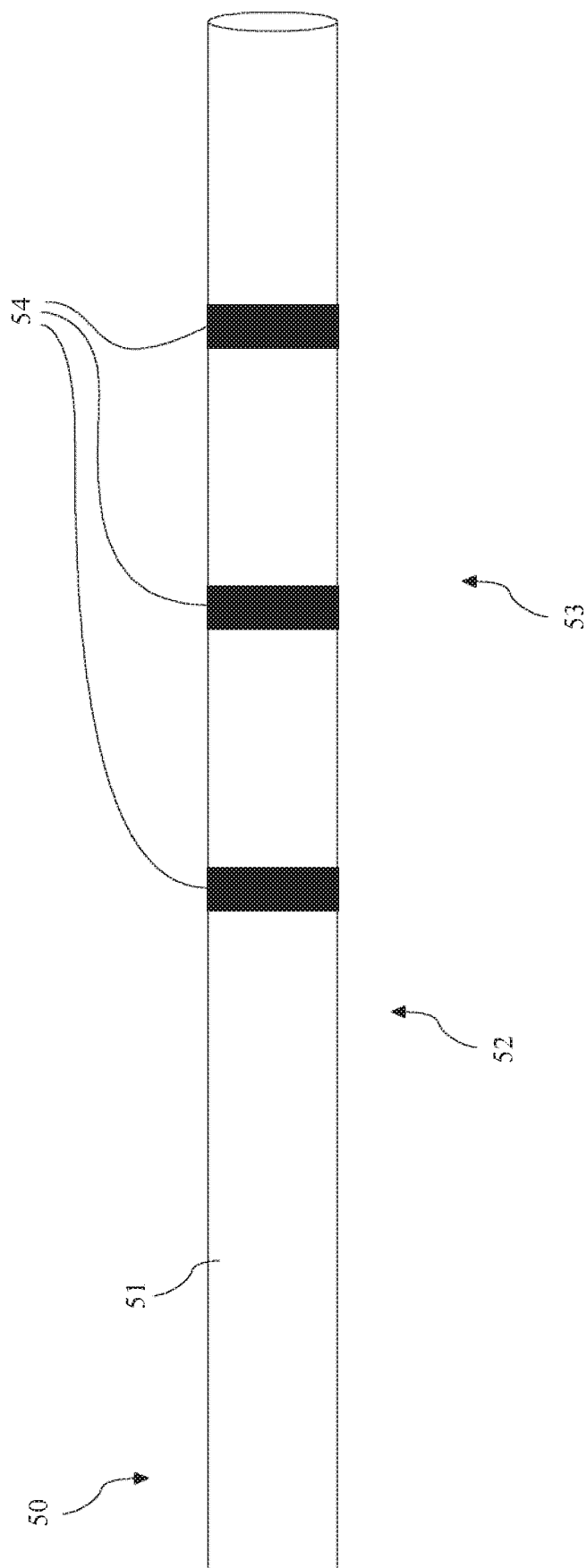
FIG. 5 depicts a detail view of a distal end of an example embodiment of a guidewire wherein the distal end comprises a measurement segment having grooves filled with a radiolucent material.

FIG. 5 depicts an example embodiment of a guidewire (50). FIG. 5 shows an enlarged view of a distal end (52) of a wire body (51) of the guidewire (50). The distal end (52) includes a measurement segment (53). The measurement segment (53) includes one or more grooves (54). In the illustrated embodiment, the grooves (54) are at least partially filled with radiolucent material to act as markers under fluoroscopy or x-ray.

Figure 6:
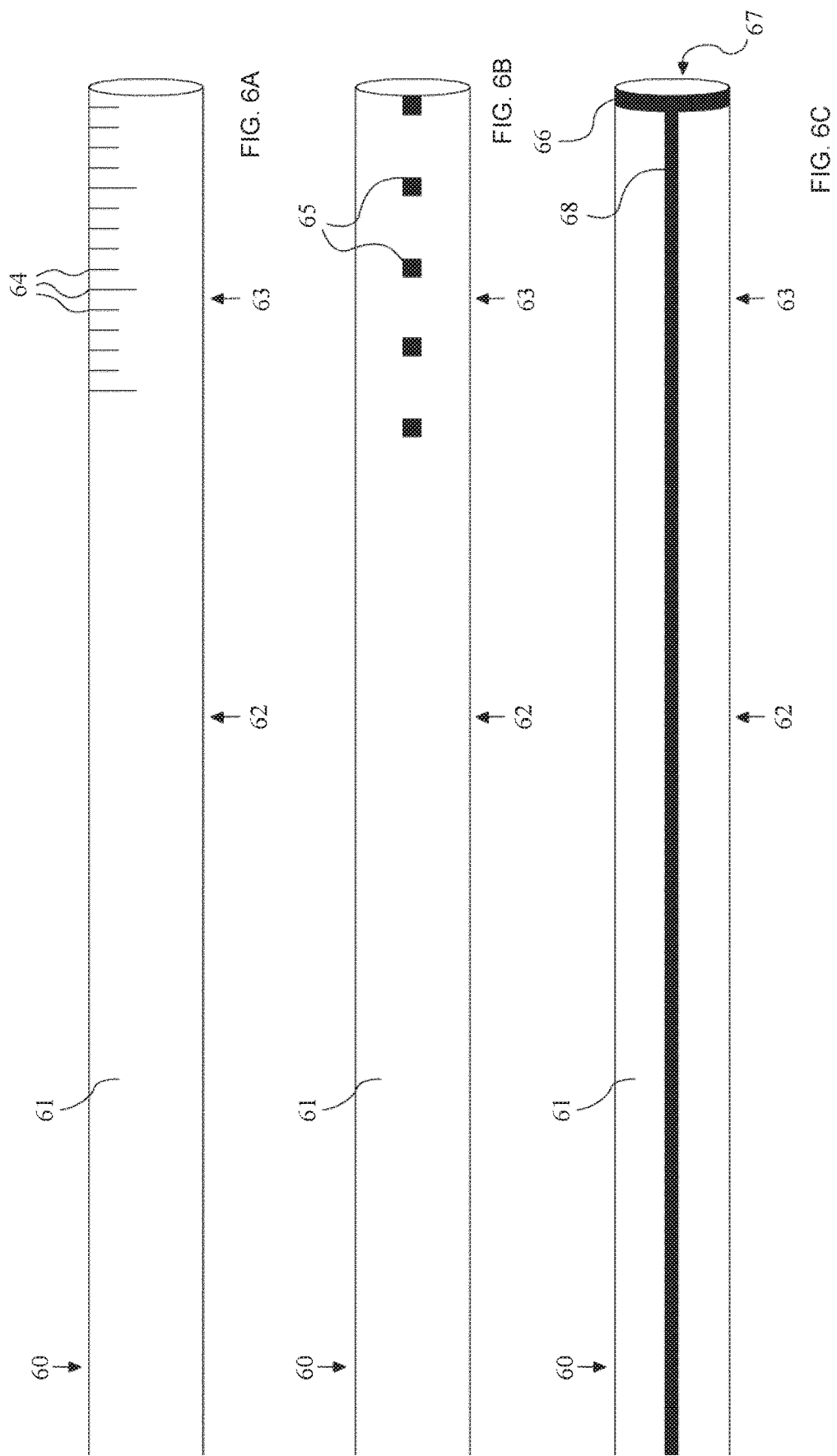
FIG. 6 depicts detail views of distal ends of several example embodiments of guidewires wherein the guidewire is composed of a radiolucent material and includes a measurement segment comprising one or more radiopaque markers on the distal end, tip, and/or entire length of the wire.

FIG. 6 depicts multiple example embodiments of a guidewire (60). FIG. 6 shows enlarged views of a distal end (62) of a wire body (61) of the guidewire (60). The guidewire (60) is made of or includes a radiolucent material. The distal end (62) includes a measurement segment (63). Radiopaque materials used in tandem with fluoroscopy or x-ray are very common in surgical tools for minimally invasive surgeries. When multiple radiopaque tools are being used at the same surgical site, the fluoroscopy or x-ray images can get crowded and make it difficult to visualize individual structures or instruments. One embodiment of the guidewire (60) (as shown in FIG. 6A), made from a radiolucent material, includes incremental radiopaque markers (64) of various sizes. The markers (64) can look and act similar to those on a ruler. Another embodiment of the guidewire (60) (as shown in FIG. 6B), made from a radiolucent material, includes incremental radiopaque markers (65). The radiopaque markers (65) may be, but are not limited to, square, rectangular, cylindrical, oval, triangular, trapezoidal, pentagonal, or hexagonal in shape. Yet another embodiment of the guidewire (60) (as shown in FIG. 6C), made from a radiolucent material, includes one or more radiopaque markers (66) on or proximate the tip (67) and one or more radiopaque markers (68) along at least a portion of the length of the guidewire (60). Such a configuration can allow a user to visualize only specific features of the wire under fluoroscopy. Said radiopaque markers (68) may be, but are not limited to square, rectangular, cylindrical, oval, triangular, trapezoidal, pentagonal, or hexagonal in shape. Other arrangements and structures of radiopaque markers are also possible.

Figure 7:
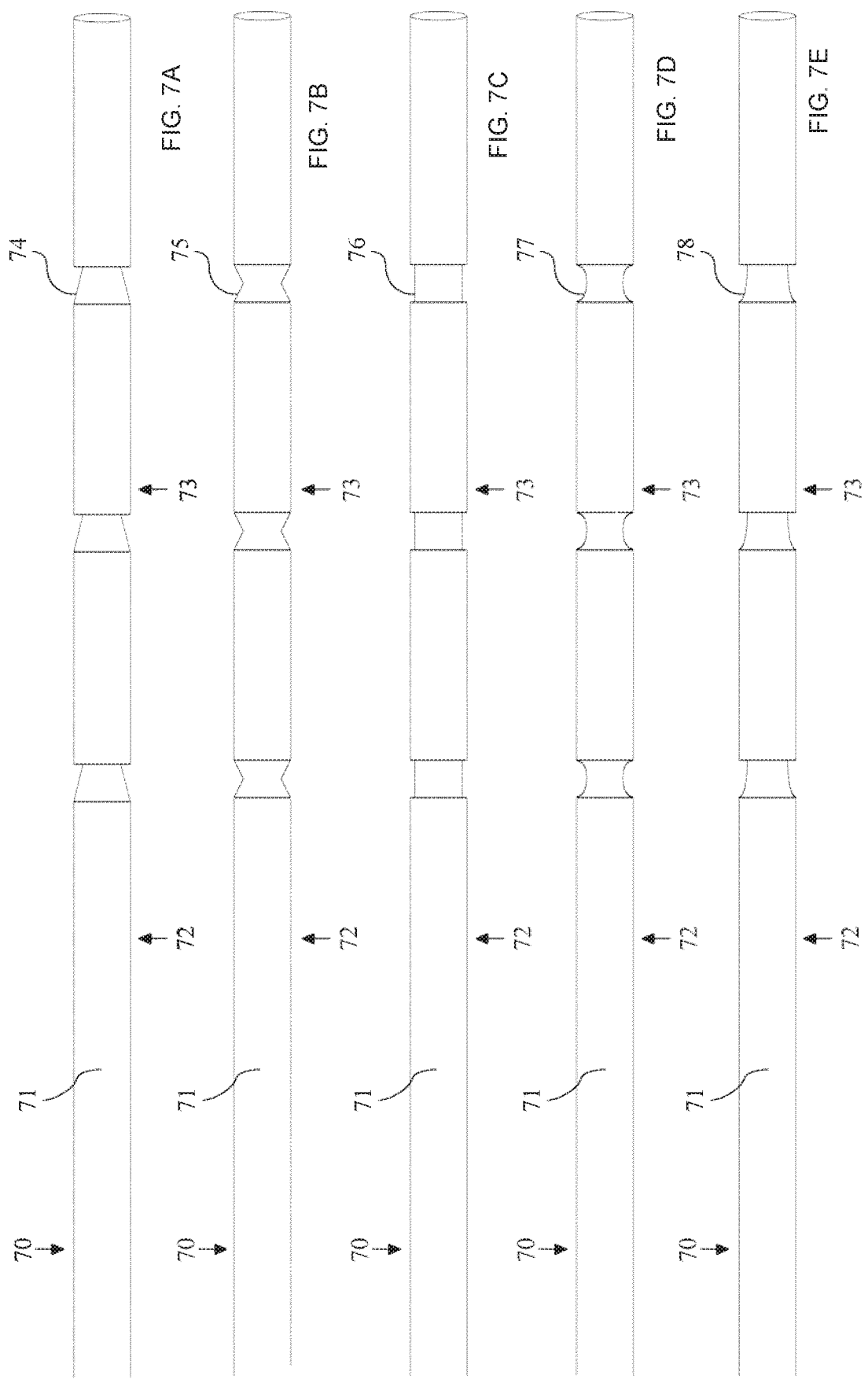
FIG. 7 depicts detail views of distal ends of several example embodiments of guidewires wherein the distal end comprises a measurement segment with grooves that may be, but are not limited to, single bevel, "V", square, "U', or" J" in shape.

FIG. 7 depicts multiple example embodiments of a guidewire (70). FIG. 7 shows enlarged views of a distal end (72) of a wire body (71) of the guidewire (70). The distal end (72) includes a measurement segment (73). In the illustrated embodiment, the measurement segment (73) includes one or more grooves. Guidewires are used for a variety of orthopedic surgeries which may require the wire to possess different strength, flexibility, safety, and/or visualization properties to fit the needs of each surgery. The method in which the grooves on the measurement segment (73) are cut plays a role in these properties. One embodiment (shown in FIG. 7A) of the guidewire (70) includes one or more single bevel grooves (74) that act as radiolucent markers under fluoroscopy or x-ray. Another embodiment of the guidewire (70) (shown in FIG. 7B) comprises one or more "V" shaped grooves (75) that act as radiolucent markers under fluoroscopy or x-ray. An embodiment of the guidewire (70) (shown in FIG. 7C) includes one or more square grooves (76) that act as radiolucent markers under fluoroscopy or x-ray. An alternative embodiment of the guidewire (70) (shown in FIG. 7D) includes one or more "U" shaped grooves (77) that act as radiolucent markers under fluoroscopy or x-ray. Yet another embodiment of the guidewire (70) (shown in FIG. 7E) includes one or more "J" shaped grooves (78) that act as radiolucent markers under fluoroscopy or x-ray. Each embodiment offers its own set of properties for strength, flexibility, safety to tissue, and their ability to be visualized under fluoroscopy or x-ray. Other groove structures or configurations are also possible.

Figure 8:
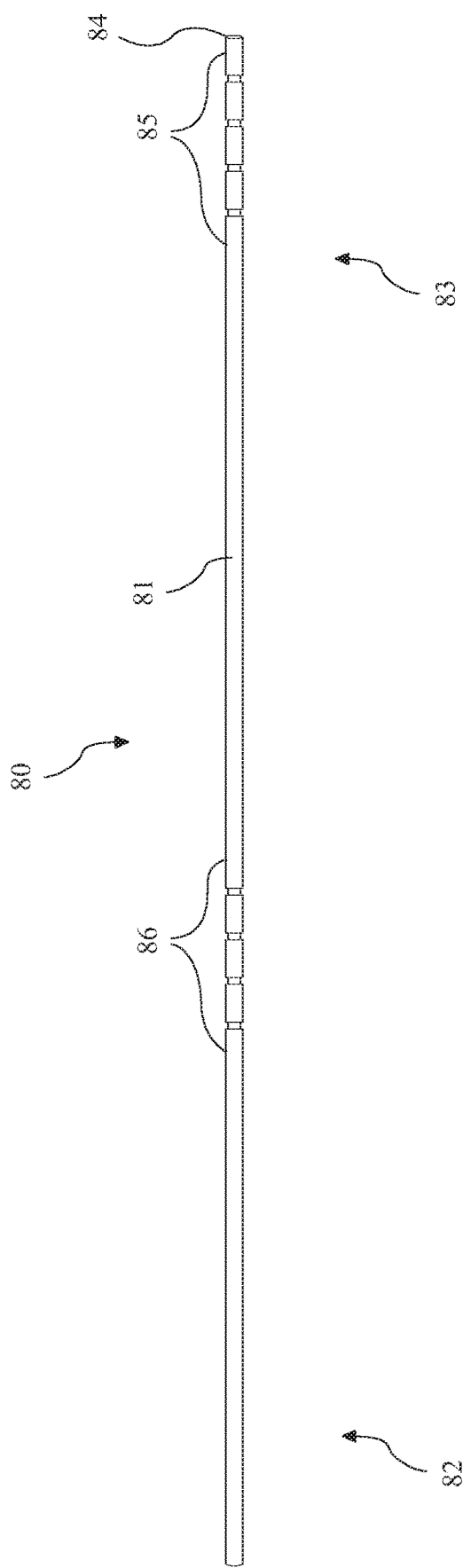
FIG. 8 depicts a full view of an example embodiment of a guidewire comprising multiple measurement segments.

FIG. 8 depicts a full view of an example embodiment of the guidewire (80) which comprises a wire body (81). Said wire body (81) has a proximal end (82) and distal end (83), wherein the distal end comprises a sharp or blunt tip (84). FIG. 8 also demonstrates a measurement segment (85) located on the distal end (83) and a second measurement segment (86) further proximally along the wire body (81). In this embodiment, both measurement segments may be used, in tandem with varying angles of fluoroscopy and x-ray imaging, to accurately measure objects and distances inside the body in any dimension.

Figure 9:
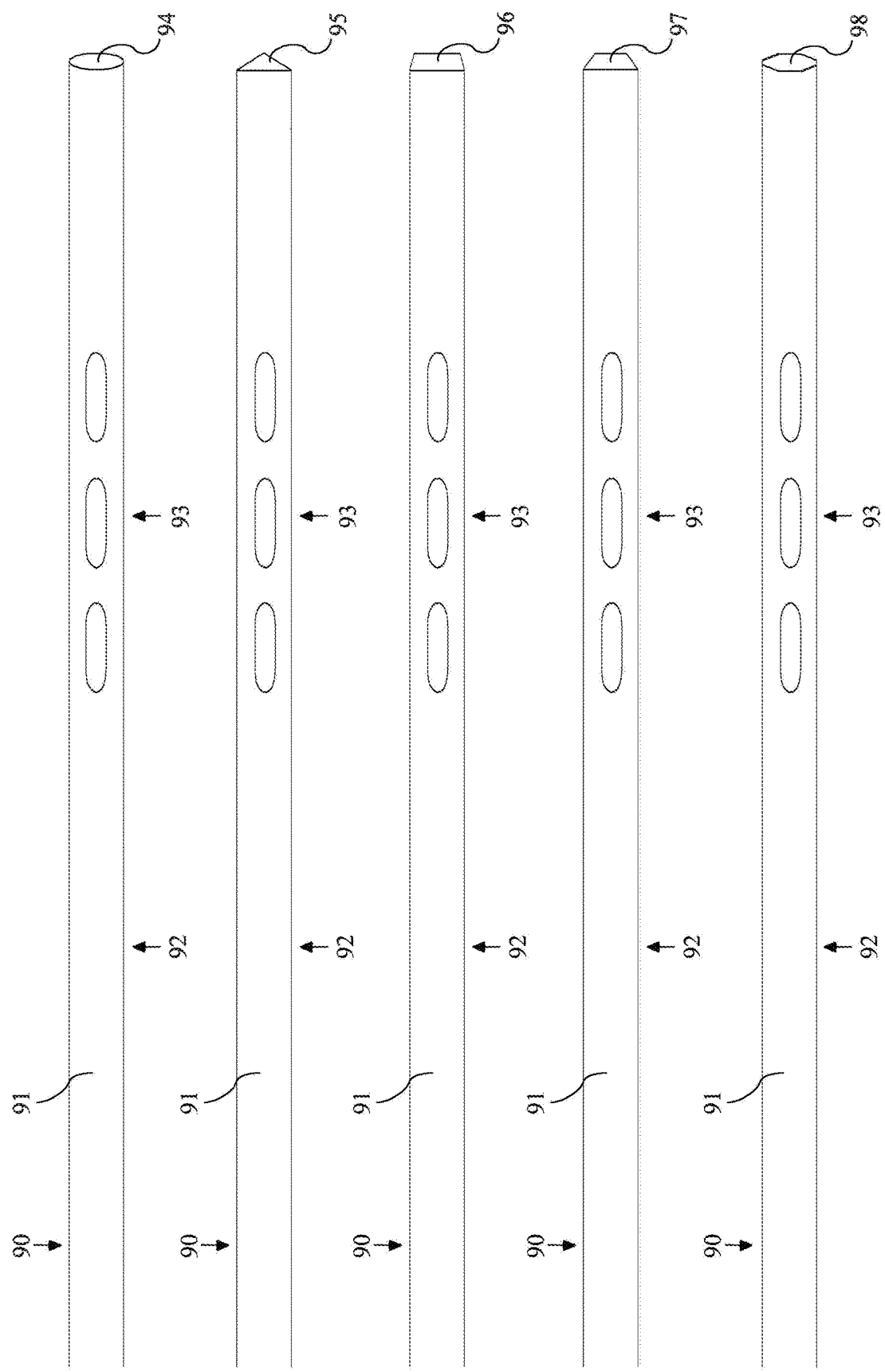
FIG. 9 depicts detail views of distal ends of several example embodiments of guidewires wherein the guidewire body may be but is not limited to, circular, triangular, square, rectangular, or hexagonal in shape.

FIG. 9 depicts multiple example embodiments of a guidewire (90). FIG. 9 shows enlarged views of a distal end (92) of a wire body (91) of the guidewire (90). The distal end (92) includes a measurement segment (93). Guidewires are used for a variety of orthopedic surgeries which may require the wire to possess different strength, flexibility, safety, and/or visualization properties to fit the needs of each surgery. The shape of the wire body (91) can play a significant role in these properties. One embodiment of the guidewire (90) depicts a wire body (91) that is circular in shape. The circular shape can be visualized at the tip (94). Another embodiment of the guide wire (90) comprises a triangular wire body (91) which may be visualized at the tip (95) as well. An embodiment of the guidewire (90) comprises a square wire body (91) which may be visualized at the tip (96). An alternative embodiment of the guide wire (90) comprises a rectangular wire body (91). The shape of the wire may be visualized best at the tip (97). Yet another embodiment of the guidewire (90) comprises a hexagonal wire body (91) which may be visualized at the tip (98) Each embodiment offers its own set of properties for strength, flexibility, safety to tissue, and their ability to be visualized under fluoroscopy or x-ray. Other wire shapes are also possible.

Figure 10:
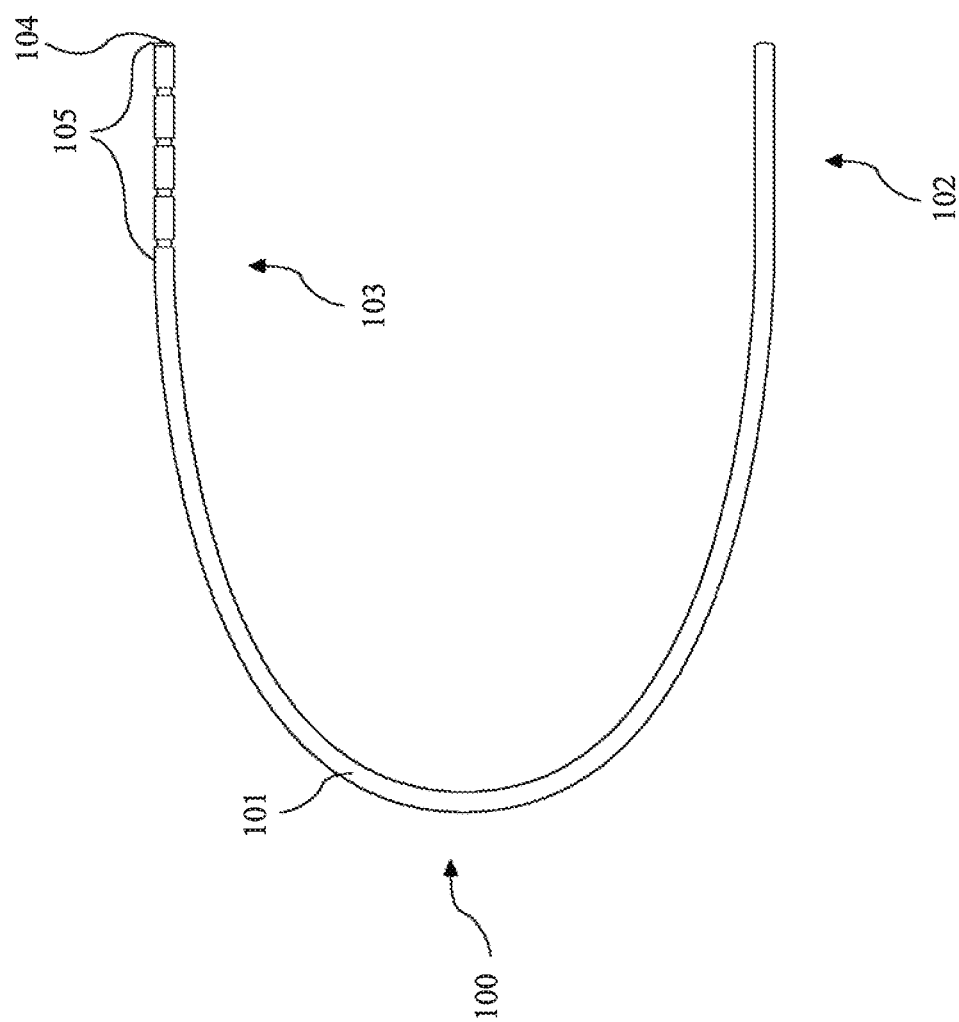
FIG. 10 depicts a full view of an example embodiment of a guidewire comprising a wire body made from nitinol that can smoothly bend without kinking.

FIG. 10 depicts a full view of an example embodiment of the guidewire (100) which comprises a wire body (101) made from a nitinol material. Said wire body (101) has a proximal end (102) and distal end (103), wherein the distal end comprises a sharp or blunt tip (104) and a measurement segment (105). FIG. 10 demonstrates the wire body's (101) ability to smoothly bend without kinking due to its nitinol composition.

Figure 11:
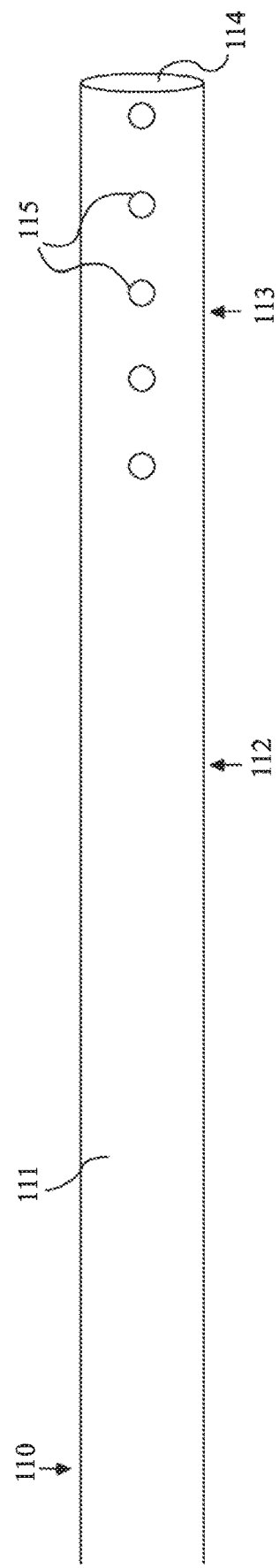
FIG. 11 depicts a detail view of a distal end of an example embodiment of a guidewire wherein the distal end comprises a measurement segment with holes that act as radiolucent markers.

FIG. 11 depicts an example embodiment of a guidewire (110). FIG. 11 shows an enlarged view of a distal end (112) of a wire body (111) of the guidewire (110). As shown, the distal end (112) includes a measurement segment (113) and tip (114). In this embodiment, the measurement segment (113) includes one or more holes (115) cut through the wire in a horizontal manner. The one or more holes (115) act as radiolucent markers under fluoroscopy or x-ray. FIG. 11 depicts the holes (115) spaced at uniform increments however in other embodiments the holes (115) may be spaced in any manner that allows the user to measure inside the body when used with x-ray or fluoroscopy. FIG. 11 also depicts the holes (115) being circular in shape, however in other embodiments the holes (115) may be oval, triangular, square, pentagonal, hexagonal or any shape that allows them to act as radiolucent markers.

Figure 12:
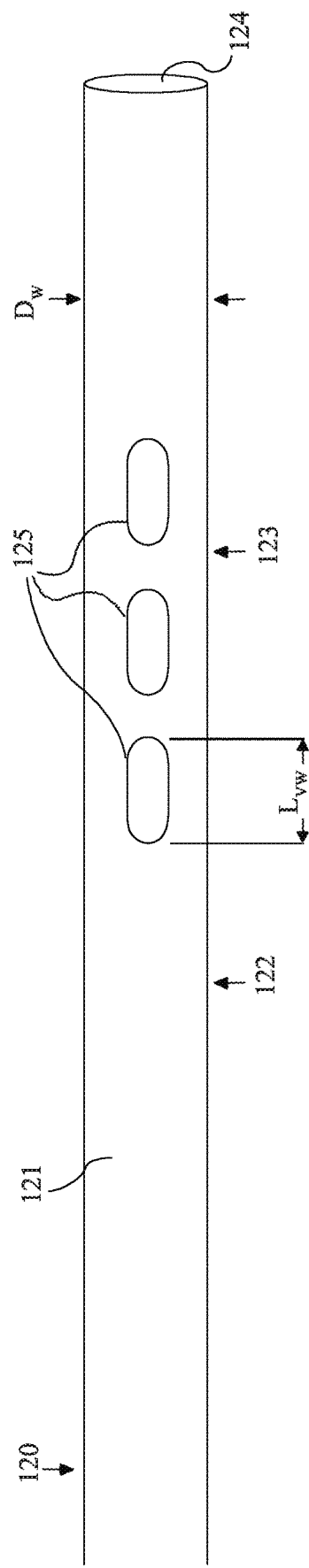
FIG. 12 depicts a detail view of a distal end of an example embodiment of a guidewire wherein the distal end comprises a measurement segment with visualization windows that act as radiolucent markers.

FIG. 12 depicts an example embodiment of a guidewire (120). FIG. 12 shows an enlarged view of a distal end (122) of a wire body (121) of the guidewire (120). As shown, the distal end (122) includes a measurement segment (123) and tip (124). In this embodiment, the measurement segment (123) includes one or more visualization windows (125) cut through the wire in a horizontal manner. The one or more visualization windows (125) act as radiolucent markers under fluoroscopy or x-ray. FIG. 12 demonstrates one embodiment, where the visualization windows (125) are oval in shape and have a length of 6.6 $D_W \geq L_{VW} \geq 0.7\ D_W$, wherein $D_W$=Diameter of the wire body and $L_{VW}$=Length of the visualization window. This length is important for the guidewire's (120) use. If the length of the visualization window (125) is too short in respect to the wire's diameter, then the measurement segment (123) will become too brittle which greatly increases the chances of it breaking. If the length of the visualization window (125) is too long in respect to the wire's diameter, then the measurement segment (123) will become too flexible to be pushed through tissue. FIG. 12 depicts the visualization windows (125) spaced at uniform increments however in other embodiments the visualization windows (125) may be spaced in any manner that allows the user to measure inside the body when used with x-ray or fluoroscopy. FIG. 12 also depicts the visualization windows (125) being oval in shape, however in other embodiments the visualization windows (125) may be circular, triangular, square, pentagonal, hexagonal or any shape that allows them to act as radiolucent markers.

Figure 13:
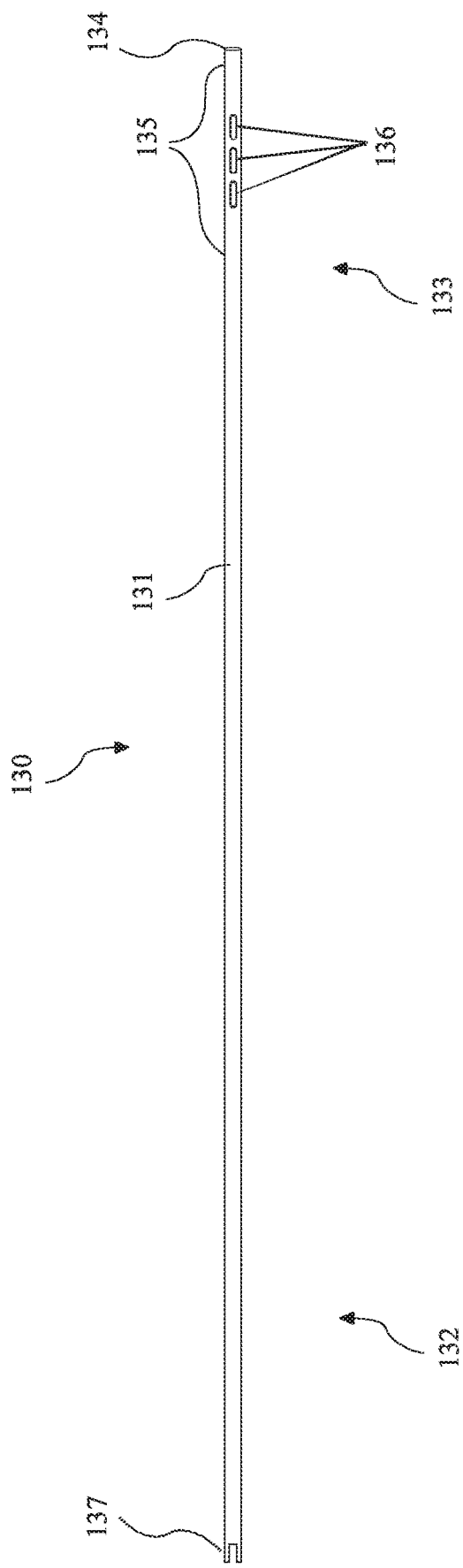
FIG. 13 depicts a full view of an example embodiment of a guidewire wherein the distal end comprises a measurement segment with visualization windows that act as radiolucent markers and the proximal end comprises an alignment aid.

FIG. 13 depicts a full view of an example embodiment of a guidewire (130). The guidewire (130) may be used during many types of orthopedic surgeries to act as a guide to the surgical site. The guidewire (130) comprises a wire body (131). The wire body (131) has a proximal end (132) and distal end (133). As shown, the distal end (133) includes a measurement segment (135) and tip (134). In this embodiment, the measurement segment (135) includes one or more visualization windows (136) cut through the wire in a horizontal manner. The one or more visualization windows (136) act as radiolucent markers under fluoroscopy or x-ray. The proximal end (132) includes an alignment guide (137) that is intended to remain outside the patient's body to allow the user to align the visualization windows (136) with the fluoroscopy or x-ray source. In some embodiments such as FIG. 13, the alignment guide (137) is necessary because the visualization windows can only be seen if they are facing the correct directions. In other embodiments not shown, the visualization windows may be placed in varying orientations so alignment of the wire is not necessary for visualization. FIG. 13 depicts the alignment guide (137) as a small split in the proximal end (132) but it should be noted that in other embodiments, the alignment guide may be, but is not limited to coloring on the wire, a machined groove, laser cut markings, etc. FIG. 13 also depicts the visualization windows (136) spaced at uniform increments however in other embodiments the visualization windows (136) may be spaced in any manner that allows the user to measure inside the body when used with x-ray or fluoroscopy. FIG. 13 also depicts the visualization windows (136) being oval in shape, however in other embodiments the visualization windows (136) may be circular, triangular, square, pentagonal, hexagonal or any shape that allows them to act as radiolucent markers.

Guidewires according to the present disclosure, such as guidewires 10, 20, 30, 40, 50, 60, 70, 80, 90, 100, 110, 120, 130 can be used in various orthopedic procedures. In an example orthopedic procedure, such as the placement of a pedicle screw, the measurement segment (e.g., measurement segment 14, 23, 33, 43, 53, 63, 73, 85, 93, 105, 113, 123, 135) in tandem with fluoroscopy, x-ray, or other imaging modalities can act as a ruler to measure what size screw is needed. In this example surgery, the measurement segment (14, 23, 33, 43, 53, 63, 73, 85, 93, 105, 113, 123, 135) allows the user to be more precise when choosing a correctly sized screw. Increased accuracy in this process leads to reduced radiation exposure for everyone in the operating room, decreased costs of surgery, quicker recovery for the patient, and a higher chance for a successful surgery.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations, one or more features from a claimed combination can, in some cases, be excised from the combination, and the combination may be claimed as a sub combination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An orthopedic guidewire comprising:
a wire body comprising a proximal end and a distal end wherein the wire body is configured to fit inside a lumen of a separately provided orthopedic implant or instrument so the implant or instrument may be guided along the orthopedic guidewire into the surgical site;
the wire body being capable of being grasped by wire holding forceps and the wire holding forceps are capable of receiving a blunt force;
a tip located on the distal end of the wire body; and
one or more measurement segments located on the wire body, the one or more measurement segments comprising one or more markers configured to be visualized under fluoroscopy or x-ray imaging, wherein the orthopedic guidewire can smoothly bend without kinking, is rigid enough to withstand the blunt force put on it by an orthopedic procedure, and the one or more markers are visualization windows.

2. The orthopedic guidewire of claim 1, wherein the wire body is circular in shape.

3. The orthopedic guidewire of claim 1, wherein the tip is rounded.

4. The orthopedic guidewire of claim 1, wherein the measurement segment is configured to measure objects and/or distances inside a patient's body when used in tandem with fluoroscopy or x-ray imaging.

5. The orthopedic guidewire of claim 1, wherein the one or more measurement segments extend along a portion of a length of the wire body.

6. The orthopedic guidewire of claim 1, wherein the one or more measurement segments extend along an entire length of the wire body.

7. The orthopedic guidewire of claim 1, wherein the wire body is comprised of a radiopaque material.

8. The orthopedic guidewire of claim 7, wherein the one or more markers are radiolucent visualization windows which can be visualized under fluoroscopy or x-ray imaging.

9. The orthopedic guidewire of claim 8, wherein the visualization windows are at least partially filled with a radiolucent material.

10. The orthopedic guidewire of claim 1, wherein the measurement segment is configured to be used to accurately estimate length, width, and/or depth when used with varying angles of fluoroscopy and/or x-ray imaging.

11. The orthopedic guidewire of claim 8, wherein the orthopedic guidewire is made of nitinol.

12. The orthopedic guidewire of claim 11, wherein the diameter of the wire is less than or equal to 0.062 inches.

13. The orthopedic guidewire of claim 12, wherein the visualization window has a length in the range of $6.6\ Dw > Lvw > 0.7\ Dw$, wherein $Dw$=Diameter of the wire body and $Lvw$=Length of the visualization window.

14. A radiopaque nitinol orthopedic guidewire comprising:
- a wire body comprising a proximal end and a distal end site;
- the wire body being capable of being grasped by wire holding forceps and the wire holding forceps are capable of receiving a blunt force;
- a tip located on the distal end of the wire body; and
- a measurement segment located on the wire body, the measurement segments comprising one or more visualization windows configured to be visualized under fluoroscopy or x-ray imaging, wherein the orthopedic guidewire can smoothly bend without kinking, is rigid enough to withstand the blunt force put on it by an orthopedic procedure, and the one or more markers are visualization windows.

15. The orthopedic guidewire of claim 14, wherein the wire body is configured to fit inside the lumen of a separately provided orthopedic implant or instrument so the implant or instrument may be guided along the orthopedic guidewire into the surgical site.

16. The orthopedic guidewire of claim 14, wherein the tip is rounded.

17. The orthopedic guidewire of claim 14, wherein the measurement segment is configured to measure objects and/or distances inside a patient's body when used in tandem with fluoroscopy or x-ray imaging.

18. The orthopedic guidewire of claim 14, wherein the visualization windows are oval shaped.

19. The orthopedic guidewire of claim 14, wherein the visualization windows are between 1-10 mm in length.

20. The orthopedic guidewire of claim 19, wherein the visualization windows span at least 10% of the wire body's diameter.

21. A method of determining the correct implant size during orthopedic surgery, the method comprising:
- providing an orthopedic guidewire comprising:
  - a wire body comprising a proximal end and a distal end and having one or more variable dimensions, rigidities, and/or radiodensities site, wherein the wire body is capable of being grasped by wire holding forceps and the wire holding forceps being capable of receiving a blunt force;
  - a tip located on the distal end of the wire body; and
  - a measurement segment, located on the wire body, comprising one or more markers configured to be visualized under fluoroscopy or x-ray imaging, wherein the one or more markers are visualization windows;
- inserting the orthopedic guidewire into the desired position inside the patient; and
- with the measurement segment in tandem with fluoroscopy or x-ray imaging, determining the correct implant size, wherein the orthopedic guidewire can smoothly bend without kinking and is rigid enough to withstand the blunt force put on it by an orthopedic procedure.

22. The method of claim 21, further comprising adjusting and temporarily positioning the orthopedic guidewire at the surgical site in a desired orientation and location.

23. The method of claim 21, further comprising inserting the proximal end of the orthopedic guidewire into a lumen of an implant or instrument and progressing an implant or instrument distally along the guidewire until in a desired location.

24. The method of claim 21, wherein the orthopedic guidewire is comprised of a radiopaque nitinol material.

25. The method of claim 24, wherein the one or more markers of the measurement segment are configured as visualization windows which may be visualized under fluoroscopy or x-ray imaging.

26. The method of claim 25, wherein the visualization window has a length in the range of 6.6 $D_w > L_{vw} > 0.7\ D_w$, wherein $D_w$=Diameter of the wire body and $L_{vw}$=Length of the visualization window.

27. The method of claim 21, further comprising removing the orthopedic guidewire from the desired location.

28. The method of claim 21, wherein the orthopedic guidewire is configured to be used to measure length, width, and/or depth when used in tandem with varying angles of separately provided fluoroscopy and x-ray imaging.

29. The method of claim 21, wherein positioning the orthopedic guidewire comprises using at least one separately provided orthopedic instrument.

30. The method of claim 29, wherein the at least one orthopedic instrument comprises a jamshidi needle.

31. The method of claim 29, wherein the at least one orthopedic instrument comprises the wire holding forceps and the mallet.

\* \* \* \* \*